US00PP22737P2

(12) United States Plant Patent
Dümmen

(10) Patent No.: US PP22,737 P2
(45) Date of Patent: May 15, 2012

(54) *PELARGONIUM* PLANT NAMED 'DUEROBINA'

(50) Latin Name: *Pelargonium zonale*
Varietal Denomination: Duerobina

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 12/928,562

(22) Filed: Dec. 14, 2010

(51) Int. Cl.
*A01H 5/00* (2006.01)

(52) U.S. Cl. ..... Plt./330

(58) Field of Classification Search ..... Plt./330
See application file for complete search history.

*Primary Examiner* — Kent L Bell
(74) *Attorney, Agent, or Firm* — C. A. Whealy

(57) ABSTRACT

A new and distinct cultivar of Zonal Geranium plant named 'Duerobina', characterized by its upright to outwardly spreading plant habit; moderately vigorous growth habit; freely basal branching habit; leaves with a distinct zonation pattern; freely flowering habit; semi-double bright red-colored flowers; and good garden performance.

1 Drawing Sheet

Botanical designation: *Pelargonium zonale.*
Cultivar denomination: 'DUEROBINA'.

BACKGROUND OF THE INVENTION

The present invention relates to a new and distinct cultivar of Zonal Geranium plant, botanically known as *Pelargonium zonale* and hereinafter referred to by the name 'Duerobina'.

The new Zonal Geranium plant is a product of a planned breeding program conducted by the Inventor in Rheinberg, Germany. The objective of the breeding program is to create new uniform Zonal Geranium plants with dark green-colored leaves and attractive flowers.

The new Zonal Geranium plant originated from a cross-pollination made by the Inventor in May, 2007 in Rheinberg, Germany of a proprietary selection of *Pelargonium zonale* identified as code number Z05-2502-4, not patented, as the female, or seed, parent with a proprietary selection of *Pelargonium zonale* identified as code number F-20-418, not patented, as the male, or pollen, parent. The new Zonal Geranium plant was discovered and selected by the Inventor as a single flowering plant from within the progeny of the stated cross-pollination in a controlled greenhouse environment in Rheinberg, Germany in May, 2010.

Asexual reproduction of the new Zonal Geranium plant by vegetative terminal cuttings in a controlled greenhouse environment in Rheinberg, Germany since May, 2010 has shown that the unique features of this new Zonal Geranium plant are stable and reproduced true to type in successive generations.

SUMMARY OF THE INVENTION

Plants of the new Zonal Geranium have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Duerobina'. These characteristics in combination distinguish 'Duerobina' as a new and distinct Zonal Geranium plant:

1. Upright to outwardly spreading plant habit.
2. Moderately vigorous growth habit.
3. Freely basal branching habit.
4. Leaves with a distinct zonation pattern.
5. Freely flowering habit.
6. Semi-double bright red-colored flowers.
7. Good garden performance.

Plants of the new Zonal Geranium differ primarily from plants of the female parent selection in branching habit as plants of the new Zonal Geranium are more freely branching than plants of the female parent selection. In addition, plants of the new Zonal Geranium have lighter green-colored leaves than plants of the female parent selection.

Plants of the new Zonal Geranium differ primarily from plants of the male parent selection in branching habit as plants of the new Zonal Geranium are more freely branching than plants of the male parent selection. In addition, plants of the new Zonal Geranium and the male parent selection differ in flower color as plants of the male parent selection have purple-colored flowers.

Plants of the new Zonal Geranium can be compared to plants of *Pelargonium zonale* 'Gentred', disclosed in U.S. Plant Pat. No. 19,134. In side-by-side comparisons conducted in Rheinberg, Germany plants of the new Zonal Geranium differed primarily from plants of 'Gentred' in the following characteristics:

1. Plants of the new Zonal Geranium were more freely branching than plants of 'Gentred'.
2. Leaves of plants of the new Zonal Geranium had a more distinct zonation pattern than leaves of plants of 'Gentred'.
3. Flowers of plants of the new Zonal Geranium were lighter red in color than flowers of plants of 'Gentred'.
4. Flowers of plants of the new Zonal Geranium had more petaloids than flowers of plants of 'Gentred'.

BRIEF DESCRIPTION OF THE PHOTOGRAPH

The accompanying colored photograph illustrates the overall appearance of the new Zonal Geranium plant showing the colors as true as it is reasonably possible to obtain in colored reproductions of this type. Colors in the photograph may differ slightly from the color values cited in the detailed botanical description which accurately describe the colors of the new Zonal Geranium plant. The photograph comprises a side perspective view of a typical flowering plant of 'Duerobina' grown in a container.

DETAILED BOTANICAL DESCRIPTION

The aforementioned photograph and following observations and measurements describe plants grown during the summer in 10.5-cm containers in a glass-covered greenhouse in Rheinberg, Germany and under conditions which closely approximate commercial production. During the production of the plants, day and night temperatures averaged 18° C. and light levels averaged 4,500 lux. Plants were pinched one time three weeks after planting and were 13 weeks old when the photograph and the description were taken. In the detailed description, color references are made to The Royal Horticultural Society Colour Chart, 1995 Edition, except where general terms of ordinary dictionary significance are used.

Botanical classification: *Pelargonium zonale* 'Duerobina'.

Parentage:

*Female, or seed, parent*.—Proprietary selection of *Pelargonium zonale* identified as code number Z05-2502-4, not patented.

*Male or pollen parent*.—Proprietary selection of *Pelargonium zonale* identified as code number F-20-418, not patented.

Propagation:

*Type*.—By vegetative terminal cuttings.

*Time to initiate roots, summer*.—About five days at temperatures of 20° C.

*Time to initiate roots, winter*.—About seven days at temperatures of 20° C.

*Time to produce a rooted young plant, summer*.—About three weeks at temperatures of 20° C.

*Time to produce a rooted young plant, winter*.—About four weeks at temperatures of 20° C.

*Root description*.—Fine, fibrous; white in color.

*Rooting habit*.—Freely branching; dense.

Plant description:

*General appearance*.—Upright to outwardly spreading plant habit; uniformly rounded; densely foliated.

*Growth and branching habit*.—Moderately vigorous growth habit; freely basal branching habit with about three basal branches developing per plant; pinching enhances lateral branch development.

*Plant height to top of flower umbels*.—About 27 cm.

*Plant height to top of foliar plane*.—About 21 cm.

*Plant width*.—About 20 cm.

*Lateral branches*.—Length: About 6 cm. Diameter: About 6.5 mm. Internode length: About 1.3 cm. Texture: Pubescent. Strength: Moderately strong. Color: Close to 144A.

Foliage description:

*Arrangement*.—Alternate; simple.

*Length*.—About 3.8 cm.

*Width*.—About 6 cm.

*Shape*.—Reniform.

*Apex*.—Acute.

*Base*.—Cordate.

*Margin*.—Crenate.

*Venation pattern*.—Palmate.

*Texture, upper surface*.—Pubescent.

*Texture, lower surface*.—Smooth, glabrous.

*Color*.—Developing and fully expanded leaves, upper surface: Close to 137C; venation, close to 143B. Developing and fully expanded leaves, lower surface: Close to 143C; venation, close to 143C.

*Zonation pattern*.—Distinct. Distance from margin: About 5 mm. Width: About 1.2 cm. Color: Close to 147A.

*Petiole*.—Length: About 5.4 cm. Diameter: About 2.6 mm. Texture, upper and lower surfaces: Smooth, glabrous. Color, upper and lower surfaces: Close to 143B.

Flower description:

*Flower arrangement*.—Semi-double flowers arranged in rounded hemispherical umbels arising from apical leaf axils; umbels displayed above the foliage on moderately strong peduncles; flowers face mostly upright to outward.

*Fragrance*.—None detected.

*Quantity of flowers*.—Freely flowering habit; about 15 flowers and flower buds per umbel with about 90 flowers per plant.

*Flowering season*.—Year-round under greenhouse conditions; in outdoor nurseries and gardens in Germany flowering is continuous from spring throughout the summer; plants begin flowering about eight weeks after planting.

*Flower longevity*.—Individual flowers last about five to seven days on the plant; flowers persistent.

*Umbel height*.—About 4.5 cm.

*Umbel diameter*.—About 6.8 cm.

*Flower diameter*.—About 4.7 cm by 4.5 cm.

*Flower depth (height)*.—About 2.1 cm.

*Flower buds*.—Length: About 1.1 cm. Diameter: About 8.5 mm. Shape: Ovoid. Color: Close to 67A.

*Petals*.—Quantity per flower: About five in a single whorl. Length: About 2.5 cm. Width: About 2.1 cm. Shape: Obovate. Apex: Rounded. Base: Attenuate. Margin: Sinuate. Texture, upper and lower surfaces: Smooth, glabrous. Color: When opening and fully opened, upper surface: Close to 44B; color becoming closer to 45D with development. When opening and fully opened, lower surface: Close to 44C; color becoming closer to 45D with development.

*Petaloids*.—Quantity per flower: About eight to eleven. Length: About 2 cm. Width: About 1.8 cm. Shape: Obovate. Apex: Rounded. Base: Attenuate. Margin: Sinuate. Texture, upper and lower surfaces: Smooth, glabrous. Color: When opening and fully opened, upper surface: Close to 44B. When opening and fully opened, lower surface: Close to 44C.

*Sepals*.—Quantity per flower: About six arranged in a single whorl. Length: About 1.1 cm. Width: About 3.75 mm. Shape: Ensiform. Apex: Acuminate. Base: Acute. Margin: Entire. Texture, upper and lower surfaces: Smooth, glabrous. Color, upper and lower surfaces: Close to 149B.

*Peduncle (umbel stem)*.—Length: About 10 cm. Diameter: About 3 mm. Strength: Moderately strong. Texture: Smooth, glabrous. Color: Close to 144A.

*Pedicel (individual flower stem)*.—Length: About 1.9 cm. Diameter: About 1.5 mm. Strength: Moderately strong. Texture: Smooth, glabrous. Color: Close to 182A.

*Reproductive organs*.—Androecium: Stamen quantity per flower: About nine. Filament length: About 6.7 mm. Filament color: Close to 155B. Anther length: About 2 mm. Anther shape: Oval. Anther color: Close to 48C. Pollen amount: Moderate. Pollen color: Close to 28A. Gynoecium: Pistil quantity per flower: One. Pistil length: About 1 cm. Stigma shape: Parted. Stigma color: Close to 45C. Style length: About 2 mm. Style color: Close to 46D. Ovary color: Close to 144A.

*Seed/fruit*.—Seed and fruit development have not been observed.

Disease/pest resistance: Plants of the new Zonal Geranium have not been observed to be resistant to pathogens and pests common to Zonal Geraniums.

Garden performance: Plants of the new Zonal Geranium have been observed to tolerate rain, wind, and temperatures ranging from about 5° C. to about 40° C. and have demonstrated good garden performance.

It is claimed:

1. A new and distinct Zonal Geranium plant named 'Duerobina' as illustrated and described.

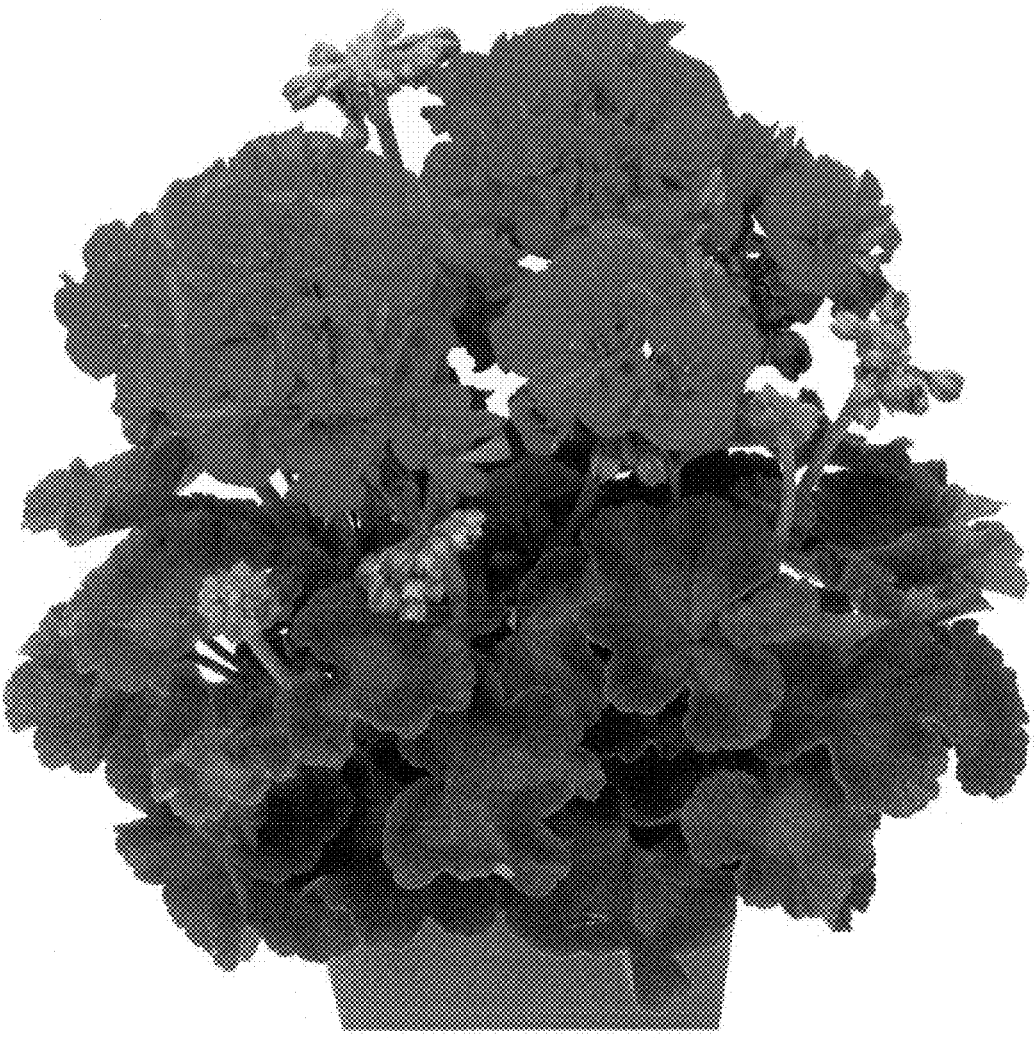

* * * * *